United States Patent [19]

Stem et al.

[11] Patent Number: 4,717,784
[45] Date of Patent: Jan. 5, 1988

[54] TOTAL ISOMERIZATION PROCESS WITH MONO-METHYL-BRANCHED PLUS NORMAL PARAFFIN RECYCLE STREAM

[75] Inventors: Stephen C. Stem; Wayne E. Evans, both of Houston, Tex.

[73] Assignee: Shell Oil Company, Houston, Tex.

[21] Appl. No.: 940,383

[22] Filed: Dec. 10, 1986

[51] Int. Cl.⁴ .............................................. C07C 5/27
[52] U.S. Cl. ................................... 585/738; 585/739; 585/822; 585/823; 585/825; 208/310 Z; 423/328
[58] Field of Search ................ 423/328; 585/738, 739, 585/822, 823, 825; 208/310 Z

[56] References Cited

U.S. PATENT DOCUMENTS

| | | | |
|---|---|---|---|
| 2,918,511 | 12/1959 | Carter et al. | 585/739 |
| 2,921,104 | 1/1960 | Haensel | 585/739 |
| 2,952,630 | 9/1960 | Eggertsen et al. | 585/825 |
| 3,718,710 | 2/1973 | Quisenberry | 585/739 |
| 3,755,144 | 8/1973 | Asselin | 585/739 |
| 3,836,455 | 9/1974 | Blytas | 585/738 |
| 4,016,245 | 4/1977 | Plank et al. | 423/328 |
| 4,176,053 | 11/1979 | Holcombe | 208/310 |
| 4,210,771 | 7/1980 | Holcombe | 585/701 |
| 4,251,499 | 2/1981 | Nanne et al. | 423/329 |
| 4,476,345 | 10/1984 | Gray, Jr. et al. | 585/820 |

FOREIGN PATENT DOCUMENTS 876730 9/1961 United Kingdom ................ 585/738

Primary Examiner—Asok Pal
Attorney, Agent, or Firm—Kimbley L. Muller

[57] ABSTRACT

This invention relates to a process for the production of an isomerate gasoline blending component where the octane value of the isomerate is increased relative to the overall cost of the process. After isomerization, the separatory sieve of this invention selectively adsorbs unreacted normal paraffins and mono-methyl-branched paraffins but not di-methyl-branched paraffins. The preferred separatory sieve is ferrierite. This process is an improvement over prior Total Isomerization Processes (using a calcium-5A separatory sieve) to recycle only n-paraffins to the isomerization zone.

17 Claims, 2 Drawing Figures

TOTAL ISOMERIZATION PROCESS WITH MONO-METHYL-BRANCHED PLUS NORMAL PARAFFIN RECYCLE STREAM

FIELD OF THE INVENTION

This invention is concerned with a process for making an isomerate gasoline blending component with higher octane by increasing the proportion of di-methyl-branched paraffins in the isomerate and reducing the quantity of mono-methyl-branched parrafins in the isomerate. As a corollary, this process is concerned with a recycle stream in a Total Isomerization Process having a content of normal paraffins and also mono-methyl-branched paraffins (e.g. methylpentanes) present in the recycle stream.

As a result of pollution and environmental problems, retail gasolines in the United States will eventually have a phased down lead content. Maintenance of high octane gasolines by methods other than lead addition is of continuing interest to U.S. refiners. Two major techniques are available to acquire high octane gasoline pools without lead addition. First, hydrocarbons can be reformed in the presence of a reforming catalyst, such as a platinum-rhenium catalyst, to a high octane gasoline. Second, normal paraffins can be isomerized to branched paraffins possessing high octane qualities. This invention concerns the latter of these two processes and is an improvement over former Total Isomerization Processes. This process supplies a unique recycle stream to boost octane rating of the resultant gasoline without increasing cost and without the expense of additional hydrocarbon consumption.

From the standpoint of increasing octane, it is desirable that hydrocarbons in gasoline have maximum branching. For example, methyl pentanes have lower octane ratings than do dimethylbutanes. Thus, in a Total Isomerization Process, it is beneficial to maximize the content of the dimethylbutanes (di-branched paraffins) in the product at the expense of methylpentanes (mono-methyl-paraffins). Applicants have discovered that a means to accomplish this goal is to formulate and develop an ideal recycle stream derivative of a specific shape-selective sieve, which will enable recycle of not only normal paraffins to the isomerization zone, but also mono-methyl-branched hydrocarbons such as methylpentanes. Thus, the product stream of this type of Total Isomerization Process contains an increased proportion of dimethylbutanes, the most highly branched (and highest octane) form of $C_6$ saturates. This results in a direct octane enhancement to the resultant gasoline without an increase in cost. In refineries which restrict production of gasoline due to octane limitations, this octane enhancement could be used to increase gasoline production.

BACKGROUND OF THE INVENTION

Pertinent areas of the Classification Manual concerned with this type of invention are, among others, Class 208 subclass 310, and Class 585 subclasses 820 and 701. In Gray, Jr. et al, U.S. Pat. No. 4,476,345, an invention is disclosed in which a portion of one of the product streams in a total isomerization system is used to wash a recycle gas stream to improve the quality of the products. The molecular sieve adsorbent is selected from naturally occurring or synthetically produced three-dimensional crystalline zeolitic aluminosilicates which selectively, on the basis of molecular size, absorb normal paraffins from the isomerized product from branched chain and/or cyclic paraffins. These molecular sieves have pore diameters of about 5 Angstroms and are exemplified by a Zeolite A, which exhibits pore diameters ranging from about 3 to about 5 Angstroms. This recycle wash contains only a small amount of non-normals which enables lowering of the undesired residuals. This process recycles directly in the vapor phase in combination with the feedstock, a mixture of normals and non-normals purged from each separatory bed to another separatory bed in the system. Exemplary of this invention is the description of the drawings set forth at Column 6 lines 1 through 14.

The Gray et al disclosure is an improvement upon a Total Isomerization Process as taught in Holcombe, U.S. Pat. No. 4,210,771. This is a process for the virtually complete isomerization of normal paraffin hydrocarbons in a feedstream consisting essentially of mixed normal and branched hydrocarbons, where the feedstream is passed first through an isomerization reactor and the products therefrom passed to an adsorption section which separates normal from branched paraffins to form an isomerate having di- and mono-branched paraffins and a recycle stream of nearly pure normal paraffins. This basic process is sometimes referred to as a Total Isomerizaiton Process (TIP). The instant invention is a basic improvement upon said process.

The zeolitic molecular sieve employed in former TIP processes is any type of adsorption bed capable of selectively absorbing normal paraffins employing the molecular size and configuration of the normal paraffin molecules as a selection criteria. Particularly suitable zeolites of this type are Zeolite A and calcium exchanged Zeolite 5A. Other naturally occurring zeolite molecular sieves include chabazite and erionite. The flow scheme of the TIP process, as exemplified in Holcombe, is herein incorporated by reference as a teaching of how to operate multiple zeolite molecular sieves to achieve proper adsorption-fill and desorption purge in an operable process. In the drawing of Holcombe, the adsorption bed systems, 44, 46, 48 and 50, are comprised of calcium 5A Zeolite in the form of 1/16" cylindrical pellets. Branched paraffins flow through the adsorption bed while normal paraffins are adsorbed. After purge of the normal paraffins from the zeolitic molecular sieve, a recycle stream is formed of normal paraffins and recycle hydrogen where the recycle stream is mixed with incoming fresh feed before charge to the patentee's isomerization zone.

A second Holcombe patent, U.S. Pat. No. 4,176,053, discuses a normal paraffin-isomerization separation process. By this technique, normal paraffins are isolated from a feedstock mixture comprising normal and branched paraffins at super atmospheric pressure using an adsorption system comprising at least four fixed adsorbent beds containing a calcium 5A Angstrom molecular sieve. A stream is formed comprising vapor from void space purging of the adsorbent and feedstock containing isoparaffins and normal paraffins. The molecular sieve employed to separate normal paraffins from said stream is one which adsorbs only normal paraffins from a mixture of branched, cyclic and normal hydrocartons in order to segregate the normal paraffins from said mixture.

These patents teach that it is most advantageous to recycle normal paraffins to exhaustion. These patents also teach that the isomerate will have a certain quantity of mono-methyl-branched hydrocarbons derived from the isomerization of normal paraffins in an upstream isomerization zone. In contrast, applicants have discovered a new and more efficient Total Isomerization Process whereby both normal paraffins and mono-methyl-branched chain hydrocarbons are recycled to increase and optimize the quantity of di-branched paraffins in the isomerate. Using the specific molecular sieves of the aforementioned patents, mono-methyl-branched hydrocarbons such as methylpentanes are untrapped and are present in the product. On the other hand, by use of the select molecular sieves of the instant process, mono-methyl-branched paraffins such as methylpentanes, are absorbed in the sieve and, after desorption, along with normal paraffins, are recycled to the feedstream or to the isomerization zone, wherein normal paraffins and mono-methyl-branched hydrocarbons are isomerized to multimethyl-branched paraffins such as dimethylbutane. This process increases the degree of branching existent within the isomerate, which increases the octane number. For example, in the instant process, increased concentrations of dimethylbutanes would result from $C_6$ feeds, relative to the prior art. In summary, both the select molecular sieve of this invention and the calcium-5A sieve preferred by the patentees adsorb normal paraffins. The select molecular sieve of this invention adsorbs mono-methyl-branched paraffins while the calcium 5A sieve does not perform such an adsorption. Finally, neither the sieve of this invention nor the calcium 5A sieve absorbs dimethyl-branched paraffins, such as dimethylbutane, which is desired to be present in the isomerate of a Total Isomerization Process.

OBJECTS AND EMBODIMENTS OF THE INVENTION

An object of this invention is to provide a process with a more economically viable recycle stream in a Total Isomerization Process wherein both normal paraffins and mono-methyl-branched paraffins are recycled to the isomerization zone.

Another object of this invention is to provide a total isomerization product with a maximum content of di-methyl-branched paraffins, such as dimethyl-branched Another object of this invention is to provide a unique application of a select molecular sieve to achieve viable separation of di-methyl-branched paraffins from normal paraffins and mono-methyl-branched paraffins.

Yet another object of this invention is to provide a total isomerization product with a higher octane value.

Yet another object of this invention is to provide a process where normal hexane, in a defined feed stream, is isomerized to an isomerate product having an increased quantity of dimethylbutane and a decreased quantity of methylpentanes utilizing a select tectosilicate adsorbent having a channel size sufficient to permit entry of normal hexane, and methylpentanes but restrictive to prohibit adsorption of dimethylbutanes.

One embodiment of this invention resides in an isomerization process to produce a gasoline isomerate from a $C_6$ paraffin comprising the combinative steps of: passing said paraffin or mixture of paraffins to an isomerization zone maintained at isomerization conditions and containing an isomerization catalyst to produce an isomerization zone effluent stream comprising di-branched paraffins, mono- branched paraffins and unreacted normal paraffins; passing said isomerization zone effluent stream to a select separatory tectosilicate sieve having a channel size sufficient to permit entry of said unreacted normal paraffins and said mono-methyl-branched paraffins and restrictive to prohibit entry of said di-methyl-branched paraffins; separating with said select tectosilicate sieve said di- branched chain paraffins as an isomerate product stream from said unreacted normal paraffins and from said mono-methyl-branched paraffins at separation conditions; and recycling at least a portion of said unreacted normal paraffin and mono-methyl-branched paraffin stream as a recycle stream to said isomerization zone or to admixture with said $C_6$ normal paraffins which are passed to said isomerization zone.

Another embodiment of this invention resides in a process for the preparation of an isomerate gasoline stream which comprises: isomerizing normal hexane, and a hereinafter defined recycle stream, in the presence of an isomerization catalyst, to form an isomerization zone effluent stream comprising normal hexane, methylpentanes, and dimethyl butanes, passing said isomerization stream to a select tectosilicate having a channel size sufficient to permit entry of said normal hexane, and methylpentanes but restrictive to prohibit adsorption of said dimethylbutanes, recovering an isomerate gasoline stream comprising dimethylbutanes and a recycle stream comprising normal hexane, and methylpentanes and recycling at least a portion of said recycle stream to said isomerization zone.

BRIEF DESCRIPTION OF INVENTION

This invention is concerned with novel use of a select zeolitic adsorbent sieve having particular qualities to permit adsorption of mono-methyl-branched paraffins and normal paraffins from an admixture of normal paraffins, mono-methyl-branched paraffins and more highly branched paraffins to thereby segregate the more highly-branched paraffins from both the normal paraffins and mono-methyl-branched paraffins. This invention provides a novel recycle stream to a Total Isomerization Process whereby the recycle stream contains both normal and mono-methyl-branched paraffins in contrast to other processes which recycle only normal paraffins.

DETAILED DESCRIPTION OF THE INVENTION

The contemplated feedstream to the instant Total Isomerization Process is comprised mainly of isomeric forms of saturated hydrocarbons having $C_6$ or greater carbon atoms. These can comprise $C_6$ normal paraffins, $C_6+$ normal paraffins or mixtures of $C_6$ and $C_6+$ normal paraffins. Such feedstocks are usually derived from refinery operations and can contain quantities of $C_5-$, $C_7+$ and cyclic paraffins. Olefinic and aromatic hydrocarbons may also be present. The preferred feedstock will contain more than 25 mol % normal hexane.

The paraffins feed material is passed through an isomerization reactor having an isomerization catalyst therein. The isomerization catalyst is preferably a zeolite with a catalytic metal disposed thereon. Exemplary of such a catalyst is mordenite with platinum having a range of 0.005 wt % to 10.0 wt % with a preferred range being from 0.2 to 0.4 wt % Other zeolite molecular sieves are also viable which have a silica to alumina molar ratio of greater than 3 and less than 60 and preferably less than 15. The zeolitic molecular sieves may have many polyvalent metal cations exchanged with the sieve, such as those of the alkali metals or alkaline earth metals. The catalytic metals associated with the isomerization function are preferably noble metals from Group VIII of the Periodic Table of elements. These can be exemplified by such metals as platinum, palladium, osmium, ruthenium, etc. The isomerization catalyst can be present per se or it may be mixed with a binder material. Other equivalent isomerization catalysts can be utilized within the confines of this invention; however, the mordenite-Group VIII metal catalyst is preferred. For example, a faujasite molecular sieve may be utilized but has poorer selectivity than mordenite.

The isomerization conditions present in the isomerization zone are those selected to maximize the conversion of normal paraffins and mono-methyl-paraffins to di-methyl-branched paraffins. This type of isomerization is favored in the vapor phase with a fixed bed of isomerization catalyst. Typical operating temperatures include from 200° to 400° C. with pressures of about 10 to 40 bar. The isomerization process, which is limited in octane upgrading by thermodynamic equilibria, is frequently measured at 10 points. Even at these select conditions, the effluent from the isomerization reactor will still contain substantial (e.g. 20 to 30 wt %) normal paraffins and mono-methyl-branched paraffins which are unreacted or partially reacted due to the aforementioned equilibrium.

After isomerization, it is preferred that the total isomerization zone effluent be transmitted to a separatory adsorption zone. This separatory zone will preferably comprise 3 to 8 adsorbent beds which can be modified to operate in an adsorption/desorption mode as exemplified in U.S. Pat. No. 4,210,771, all of the teachings of which in regard to the function of the desorption/adsorption zone are herein incorporated by reference. However, in contrast to the teachings of U.S. Pat. No. 4,210,771, a unique and select molecular sieve is utilized in the adsorbing zones of this process. A calcium-5A sieve is capable of adsorbing virtually no methylpentane nor di-methylbutane while a sodium ZSM-5 molecular sieve will adsorb both methylpentane and dimethylbutane in substantial quantities.

The molecular sieve of this invention is a tectosilicate having precise channel dimensions intermediate the channel dimensions present in either the calcium-5A sieve or the ZSM-5 sieve. The molecular sieve of this invention is capable of adsorbing not only normal hexane, but methylpentanes as well. A preferred molecular sieve of this invention is a tectosilicate having channel dimensions intermediate 5.5×5.5 and 4.5×4.5, but excluding 4.5×4.5 (i.e. calcium 5A) Angstroms.

A most preferred molecular sieve is ferrierite, which exhibits greatly increased adsorption capacity toward methylpentane relative to a calcium-5A molecular sieve. It has been discovered that both the sodium and hydrogen form of ferrierite are viable although it is preferred that the ferrierite be utilized with a cation of an alkali metal, alkaline earth metal or transition metal cations. The tectosilicates of this invention include ferrierite and other analogous shape-selective materials with channel dimensions intermediate those of the calcium 5 A and ZSM-5 molecular sieve which selectively adsorbs methylpentanes while dimethylbutanes are excluded. Other examples of these crystalline sieves would be aluminophosphates, silicoaluminophosphates and borosilicates. It is also feasible that the instant tectosilicate could be a larger pore zeolite that has been ion exchanged with large cations so as to diminish the effective channel size of the tectosilicate to within the aforementioned range of dimensions. Thus, any tectosilicate having channel dimensions intermediate those of the calcium-5A and ZSM-5 is a candiate sieve with the potential to differentiate between methylpentanes and dimethylbutanes.

As exemplary of the type of tectosilicates which are viable for this technique, the following list is given showing the channel size dimensions of various zeolites including those preferred by former TIP processes such as chabazite, erionite, calcium-5A, etc.

TABLE 1

| Zeolite | Channel Dimensions (A) | Size |
|---|---|---|
| chabazite | 3.9 × 4.1 | TOO SMALL |
| zeolite A | 3.9 × 4.1 | TOO SMALL |
| erionite | 3.6 × 5.2 | TOO SMALL |
| Ca-5A | 4.5 × 4.5 | TOO SMALL |
| ferrierite | 4.5 × 5.5 | CORRECT SIZE |
| ZSM-5 | 5.4 × 5.6 | TOO LARGE |
| offretite | 6.0 × 6.0 | TOO LARGE |
| mordenite | 6.7 × 7.0 | TOO LARGE |
| omega | 7.4 × 7.4 | TOO LARGE |
| Y zeolite | 7.4 × 7.4 | TOO LARGE |

Zeolites that are too small in pore size do not discriminate between mono-methyl-branched $C_6$ (i.e. methylpentanes) and di-methyl-branched $C_6$ (i.e. dimethylbutanes). In fact, they exclude both. Zeolites that are listed as too large do not discriminate between monomethyl-branched and di-methyl-branched $C_6$. In fact, they adsorb both. Thus, only zeolites between, and not including, the sizes of the sieves of calcium-5A and ZSM-5 discriminate to accommodate mono-methyl-branched adsorption while excluding di-methyl-branched $C_6$ paraffins. While ferrierite is the best example of such a sieve, this invention should not be limited to ferrierite per se as the only species which is operable for this process.

The adsorption/desorption conditions typically utilized within the multiple tectosilicate sieves comprise a temperature of from about 75° C. to about 400° C. and a pressure of from about 2 bar to about 42 bar. Specific desorbents utilized in order to extract the desired trapped normal paraffin and mono-methyl-paraffins will preferably be hydrogen, which can be transferred with the normal paraffin and mono-methyl-paraffin recycle stream to the isomerization zone.

DETAILED DESCRIPTION OF THE DRAWINGS

Figure 1:
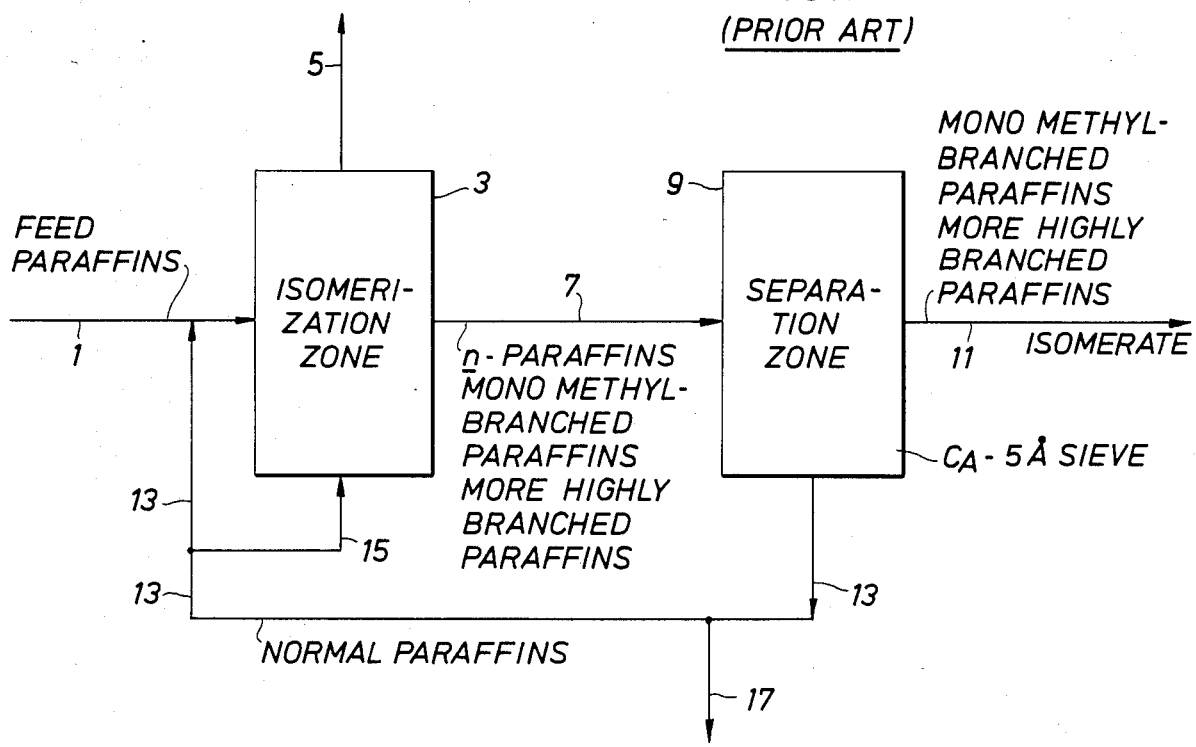
FIG. 1 is a schematic flow scheme of a Total Isomerization Process as known in the prior art.

In FIG. 1 a feedstream comprising a fresh feed having, for example, 4 mol % $C_1$ to $C_5$; and 93 mol % $C_6$ paraffins with minute quantities of cycloparaffins, aromatics, and $C_7^+$ paraffins are passed through conduit 1 into isomerization zone 3. This zone is maintained at conditions selected to maximize the quantity of di-methyl-branched paraffins from the feed material. A typical isomerization catalyst as described at Column 5 of U.S. Pat. No. 4,210,771 can be present in this prior art process. If desirable, a vented hydrogen or light hydrocarbon gas stream can be removed from the isomerization zone in conduit 5. An effluent stream from isomerization zone 3 is removed in conduit 7 containing normal paraffins, mono-methyl-branched paraffins and more highly branched paraffins (e.g. ethylpentane, dimethylbutane etc.). All of these components are transmitted to a separatory zone 9 having at least three and preferably up to 8 adsorbent beds of a molecular sieve such as a calcium-5A zeolite sieve to separate product from recycle. The calcium-5A sieve will entrap or absorb normal paraffins while allowing mono-methyl-branched paraffins and other branched paraffins to pass through the separation zone and be recovered in conduit 11 as the applicable isomerate. After applicable desorption with means not shown, a normal paraffin stream in conduit 13 is withdrawn from the separatory zone 9 and passed either to admixture with feed in conduit 1 or a portion of the same is transmitted to isomerization zone 3 by means of conduit 15. It is also preferred that some type of slipstream also be present in the recycle stream as shown in conduit 17 so as to eliminate unwanted impurities and to remove certain normal paraffins if they cannot be isomerized to exhaustion.

Figure 2:
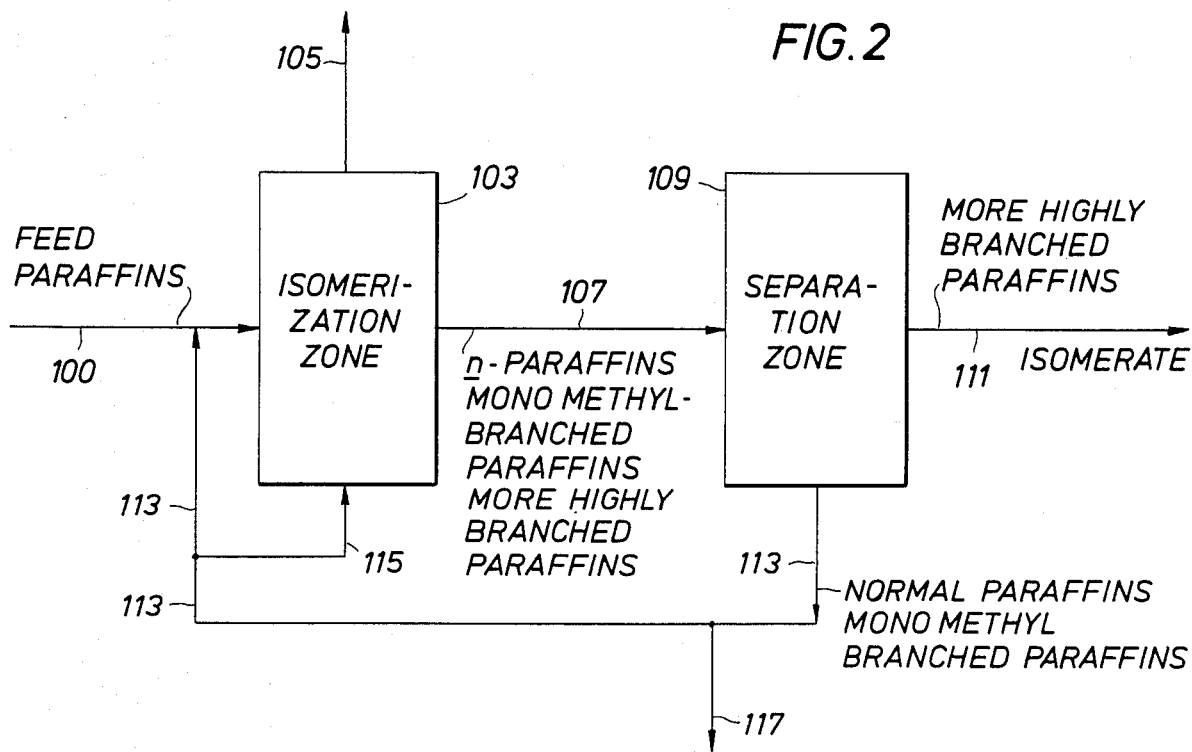
FIG. 2 is a schematic flow scheme of the novel process of this invention.

FIG. 2 demonstrates a similar feed paraffin material in conduit 100 being passed to isomerization zone 103 for the select isomerization of materials to di-branched paraffins. An off gas stream may be removed in conduit 105 with an isomerization zone effluent stream in conduit 107 containing normal paraffins, mono-methyl-branched paraffins and more highly-branched paraffins. This effluent stream is passed to a multiple separatory zone 109 which contains particular tectosilicates useful in this invention having channel dimensions intermediate 4.5×4.5 and 5.5×5.5 A. These tectosilicates may be prepared by any known ferrierite synthesis procedure such as exemplified in U.S. Pat. Nos. 4,016,245 or 4,251,499. This separatory tectosilicate sieve is selective for adsorbing or trapping normal and mono-methyl-branched paraffins. Thus, the isomerate of this invention is different from that acquired in conduit 11 of FIG. 1 in that the effluent in conduit 111 from separation zone 109 contains a greater concentration of di-methyl-branched paraffins. As a result of this different separatory function versus other TIP processes, recycle stream 113 will be very different. In fact, the difference is derivative of the presence of mono-methyl-branched paraffins in addition to the normal paraffins, all of which are recycled to feed paraffins 100 via conduit 113 or a portion of the same may be passed directly to the isomerization zone via conduit 115. A slip stream 117 may also be present to remove unwanted impurities or to extract normal paraffins and mono-methyl-branched paraffins which are not recyclable to exhaustion.

The process flow scheme of FIG. 2 demonstrates the difference in the particular recycle streams derivative of the tectosilicates used in this invention. The following examples highlight the technical advantages derivative of achieving this type of recycle.

EXAMPLES

The instant examples are given as exemplary of the instant process and should not be considered a limitation as to the broad aspects of use of a tectosilicate in a TIP process to acquire a unique recycle stream for the isomerization zone.

EXAMPLE 1

In this example, sorption capacities of sodium ferrierite, calcium-5A and sodium ZSM-5 sieves were determined in regard to normal hexane, 3-methylpentane and 2,3-dimethylbutane. The particular denoted zeolite was placed on a pan in a Cahn balance, sample chamber was evacuated, and heated to 550° C. for one hour. The particular zeolite was thus dried and following drying was cooled to 105° C. At this time, hydrocarbon vapors were admitted to the evacuated chamber to a level of 100 torr. Weight changes due to the adsorption of hydrocarbon into the zeolite were recorded. An exposure time of three hours was allowed for the branched hydrocarbons to approach equilibrium weight, whereas an exposure time of only one half hour was required for normal hexane. The results of this adsorption are shown in Table 2. Each combination of zeolite plus solvent was subjected to at least three separate determinations. Listed in the Table are results of individual determinations, as well as mean and standard deviation values for each set of determinations.

TABLE 2

| Hydrocarbon | Weight of HC Adsorbed (mg/g) | | |
|---|---|---|---|
| | Ca-5A | Na—Ferrierite | Na—ZSM-5 |
| 2,3-Dimethylbutane | 1.6 | 2.1 | 59.4 |
| | 1.3 | 1.7 | 59.7 |
| | 1.9 | 1.9 | 61.1 |
| | 2.4 | 1.8 | — |
| MEAN + STD DEV: | 1.8 ± 0.4 | 1.9 ± 0.1 | 60.0 ± 0.9 |
| 3-Methylpentane | 1.7 | 19.4 | 56.5 |
| | 1.9 | 19.6 | 63.9 |
| | 2.0 | 18.4 | 62.3 |
| | 1.5 | — | — |
| | 1.2 | — | — |
| MEAN + STD DEV: | 1.7 ± 0.3 | 19.2 ± 0.5 | 60.9 ± 3.8 |
| n-Hexane | 92.3 | 55.4 | 111.9 |
| | 90.1 | 54.5 | 105.4 |
| | 100.7 | 53.9 | 106.7 |
| | 99.3 | 56.7 | — |
| MEAN + STD DEV: | 95.6 ± 4.5 | 57.4 ± 1.0 | 107.9 ± 3.4 |

The sorption capacities are reported as weight gain in the sieve relative to the dry weight of the pure zeolite. As shown in Table 2, the calcium-5A zeolite adsorbed very little branched hydrocarbon and thus is a preferred adsorbent for the recycle of pure normal paraffins to exhaustion as exemplified in prior TIP processes. The ratio of 3-methylpentane/normal hexane sorption capacities is 0.018. In contrast, sodium ferrierite adsorbed little dimethylbutane but adsorbed a substantial amount of 3-methylpentane. The ratio of the 3-methylpentane/normal hexane sorption capacity is about 20 times greater for the sodium ferrierite than for calcium-5A zeolite. The sodium ZSM-5 sieve adsorbed virtually identical amounts of the mono- and di-branched isomers. Thus, the aforedescribed sodium ferrierite has the capability to effect a separation between 3-methylpentane and 2,3-dimethylbutane.

EXAMPLE 2

The sorption capacities of a hydrogen ferrierite towards the same three hydrocarbons were determined and are presented in Table 3. These data clearly show the comparison of the hydrogen ferrierite versus the calcium-5A zeolite. The ratio of 3-methylpentane/normal hexane sorption for the hydrogen ferrierite is about 25 times greater than that for the calcium-5A sieve. A comparision of the sodium ferrierite and hydrogen ferrierite, i.e. see Tables 2 and 3, underscores the discovery that approximately sized tectosilicates can be tailored to modify the relative sieving capabilities.

TABLE 3

| Hydrocarbon | H—Ferrierite | Ca-5A |
|---|---|---|
| 2,3-Dimethylbutane | 3.6 | 1.6 |
| | 3.3 | 1.3 |
| | 3.2 | 1.9 |
| | 3.1 | 2.4 |
| MEAN + STD DEV: | 3.3 ± 0.2 | 1.8 ± 0.4 |
| 3-Methylpentane | 28.8 | 1.7 |
| | 28.6 | 1.9 |
| | 27.1 | 2.0 |
| | 27.4 | 1.5 |
| | | 1.2 |
| MEAN + STD DEV: | 28.0 ± 0.8 | 1.7 ± 0.3 |
| n-Hexane | 56.5 | 92.3 |
| | | 90.1 |
| | | 100.7 |
| | | 99.3 |
| MEAN + STD DEV: | 56.5 | 95.6 ± 4.5 |

EXAMPLE 3

A sample of ammonium ferrierite was tableted to 14-45 mesh and placed in a glass tube. The glass tube was placed in a tube furnace under a flow of nitrogen and heated to 500° C. for 2 hours to expel ammonia and thus produce the hydrogen form of ferrierite. Under the same nitrogen flow, the molecular sieve was cooled to room temperature while the nitrogen flow was diverted through a gas saturation tower containing a mixture of normal hexane, 3-methylpentane and 2,3-dimethylbutane. The molecular sieves were exposed to hydrocarbon-containing streams of nitrogen for 1 hour. Samples of the hydrocarbon reservoir were taken at the beginning and at the end of the gas saturation period. The purpose of sampling both at the start and at the end of the experiment was to verify that the ratio of hydrocarbons remained essentially constant throughout the experiment. A portion of the hydrocarbon-containing vapor stream was diverted directly through a cold finger that was immersed in a dry ice/acetone bath to collect a sample of the actual hydrocarbon vapors.

Following exposure to these vapors, the hydrocarbon-saturated ferrierite sample was removed from the glass tube and placed on a vacuum line. The sample was evacuated to below 1 torr through a cold finger immersed in liquid nitrogen. The sample was heated to 40° C. and the sorbed hydrocarbon was quantitatively removed from the zeolite. It was experimentally determined that this first trapping was quantitative. The results of the adsorption were analyzed by gas chromatography and are shown in Table 4.

TABLE 4

Competitive Sorption of Hexane Isomers By H—Ferrierite

| Sample | % w 2,3-DMB | % w 3-MP | % w n-hexane |
|---|---|---|---|
| Gas saturation tower contents at start of experiment | 34.5 | 36.8 | 28.0 |
| Gas saturation tower contents at end of experiment | 36.5 | 36.6 | 26.3 |
| Gaseous hydrocarbon stream | 41.5 | 36.1 | 21.8 |
| Hydrocarbon adsorbed by H—ferrierite | 1.3 | 16.9 | 80.3 |

As shown in Table 4, very little dimethylbutane entered the hydrogen ferrierite. Because the adsorption capacity of normal hexane is greater than that of 3-methylpentane and because the rate of adsorption is faster for the unbranched molecules, the hydrocarbon recovered from the zeolite pores was enriched in normal hexane. A substantial amount of methylpentane was adsorbed along with the normal hexane.

We claim as our invention:

1. An isomerization process to produce a gasoline blending component from a hydrocarbon stream comprising a $C_6$ normal paraffin, $C_6^+$ normal paraffins or mixtures thereof, said process comprising the combinative steps of:

(a) passing said paraffins or mixture of paraffins to an isomerization zone maintained at isomerization conditions and containing an isomerization catalyst to produce an isomerization zone effluent stream comprising di-branched paraffins, mono-methyl-branched paraffins and unreacted normal paraffins;;

(b) passing said isomerization zone effluent stream to a select separatory tectosilicate sieve having a channel size intermediate 5.5×5.5 and 4.5×4.5 and excluding 4.5×4.5A and being sufficient to permit adsorption of said unreacted normal paraffins and said mono-methyl-branched paraffins but restrictive to prohibit adsorption of said di-branched paraffins;

(c) separating with said select tectosilicate sieve said di-branched paraffins as an isomerate product stream from said unreacted normal paraffins and from said mono-methyl-branched chain paraffins at separation conditions; and (d) recycling at least a portion of said unreacted normal paraffin and mono-methyl-branched paraffin stream to said isomerization zone or to admixture with said normal paraffin or mixture of normal paraffins, which are passed to said isomerization zone.

2. The process of claim 1 wherein said isomerization zone is maintained at a temperature of 200° C. to 400° C. and a pressure of from about 10 bar to about 40 bar.

3. The process of claim 1 wherein said isomerization catalyst comprises an aluminosilicate having a Group VIII metal deposited therewith.

4. The process of claim 3 wherein said aluminosilicate is mordenite and said Group VIII metal is platinum.

5. The process of claim 4 wherein said platinum is present in a weight concentration of from about 0.2 to about 0.4 wt %.

6. The process of claim 4 wherein said mordenite has associated therewith an inorganic binder.

7. The process of claim 1 wherein said separatory tectosilicate sieve comprises ferrierite.

8. The process of claim 1 wherein said tectosilicate sieve comprises ferrierite having cations exchanged therein selected from the group consisting of the alkali metal, alkali earth metal and transition metal cations.

9. The process of claim 1 wherein said separation conditions include a temperature of from about 75° C. to about 400° C. and a pressure of from about 2 bar to about 42 bar.

10. The process of claim 1 wherein said unreacted normal paraffin and mono-methyl-branched paraffin recycle stream is recycled to said isomerization zone or to admixture with said normal paraffin or mixture of normal paraffins in a continuous manner until said unreacted normal paraffin and mono-methyl-branched paraffins in said recycle are exhausted by conversion to di-branched paraffins.

11. The process of claim 1 wherein said isomerate product contains a predominant amount of di-methyl-branched paraffins and a diminished quantity of monomethyl-branched paraffins as a result of said tectosilicate adsorption of said mono-methyl-branched paraffins from said di-methyl-branched paraffins.

12. A process for the preparation of an isomerate gasoline blending component which comprises isomerizing normal hexane and a hereinafter defined in the presence of an isomerization catalyst, at isomerization conditions, to form an isomerization zone effluent stream comprising normal hexane, methyl pentanes, and di-methyl butane, passing said isomerization zone effluent stream to a select molecular sieve having a channel size intermediate 5.5×5.5 and 4.5×4.5 and excluding 4.5×4.5A and being sufficient to permit adsorption of said normal hexane, and methyl pentanes but restrictive to prohibit adsorption of said di-methyl butanes, recovering an isomerate gasoline blending component comprising said di-methyl butanes and a recycle stream comprising normal hexane and methyl pentanes, and recycling at least a portion of said recycle stream to said isomerization zone.

13. The process of claim 12 wherein said molecular sieve comprses ferrierite.

14. The process of claim 12 wherein said isomerization catalyst comprises a mordenite aluminosilicate having platinum dispersed thereon.

15. The process of claim 14 wherein said platinum is present in a weight content of from about 0.005 wt % platinum to about 10.0 wt % platinum.

16. The process of claim 12 wherein said isomerization catalyst comprises a Y faujausite sieve having 0.2 to 1.4 wt % platinum dispersed thereon.

17. The process of claim 12 wherein said recycle stream is passed to said isomerization zone in admixture with said normal hexane wherein said recycle stream is treated to remove at least a portion of said recycle stream from said process by means of a slipstream.

* * * * *

UNITED STATES PATENT AND TRADEMARK OFFICE
CERTIFICATE OF CORRECTION

PATENT NO. : 4,717,784
DATED : January 5, 1988
INVENTOR(S) : STEPHEN C. STEM and WAYNE E. EVANS It is certified that error appears in the above-identified patent and that said Letters Patent are hereby corrected as shown below:

In claim 12, column 11, line 6, after the word "defined" please add ---recycle stream---.

Signed and Sealed this

Nineteenth Day of July, 1988

Attest:

DONALD J. QUIGG

Attesting Officer

Commissioner of Patents and Trademarks